United States Patent [19]
Van Groningen

[11] Patent Number: 5,391,195
[45] Date of Patent: Feb. 21, 1995

[54] DEVICE FOR CARRYING OUT AN IONTOPHORESIS TREATMENT ON A PATIENT

[75] Inventor: Johannis Van Groningen, Achthuizen, Netherlands

[73] Assignee: B.V. Optische Industrie De Oude Delft, Delft, Netherlands

[21] Appl. No.: 962,196

[22] PCT Filed: Apr. 15, 1992

[86] PCT No.: PCT/NL92/00077

§ 371 Date: Feb. 8, 1993

§ 102(e) Date: Feb. 8, 1993

[87] PCT Pub. No.: WO92/18197

PCT Pub. Date: Oct. 29, 1992

[30] Foreign Application Priority Data

Apr. 17, 1991 [NL] Netherlands ............ 9100662

[51] Int. Cl.6 .............................................. A61N 1/18
[52] U.S. Cl. ........................................ 607/72; 607/75; 604/20
[58] Field of Search ............ 607/72, 75, 63; 604/20

[56] References Cited

U.S. PATENT DOCUMENTS

| | | | |
|---|---|---|---|
| 3,991,755 | 11/1976 | Vernon et al. | 604/20 |
| 4,019,510 | 4/1977 | Ellis | 604/20 |
| 4,116,238 | 9/1978 | Pettijohn | 604/20 |
| 4,141,359 | 2/1979 | Jacobsen et al. | 604/20 |
| 4,167,190 | 9/1979 | Sorenson et al. | |
| 4,340,047 | 7/1982 | Tapper et al. | 604/20 |
| 5,047,007 | 9/1991 | McNichols et al. | 604/20 |
| 5,088,977 | 2/1992 | Sibalis | 604/20 |

FOREIGN PATENT DOCUMENTS

0308572  3/1989  European Pat. Off. ............ 604/20

*Primary Examiner*—William E. Kamm
*Assistant Examiner*—Kennedy J. Schaetzle
*Attorney, Agent, or Firm*—Louis E. Marn

[57] ABSTRACT

There is disclosed a device for effecting iontophoresis treatment on a patient including a signal generator for generating the treatment signal and having an output stage including two electrodes for connecting to a patient wherein the signal generator generates a treatment signal of a pulsed direct current having a frequency of at least 1 kHz at a duty cycle of at least 80%.

5 Claims, 1 Drawing Sheet

DEVICE FOR CARRYING OUT AN IONTOPHORESIS TREATMENT ON A PATIENT

The invention relates to a device for carrying out an iontophoresis treatment on a patient, provided with a signal generator for generating a treatment signal and an output stage which can be connected to the patient by means of two electrodes.

Such devices are known in various embodiments. With the aid of an iontophoresis treatment, it is possible to introduce electrically charged particles into a patient's body by means of the treatment signal. In this way it is possible to introduce a drug locally into the body. Under these circumstances, the quantity of substance introduced into the body is essentially proportional to the product of the treatment current and the time. In the standard devices of this type, various kinds of treatment signals are used but they all have disadvantages.

A known treatment signal is formed by an uninterrupted direct current, which has the drawback that a severe burning sensation is induced in the patient by this current form, which can very rapidly result in cauterisation of the patient's skin, either over a large area under the entire electrode or as a local so-called point cauterisation. As a result, the maximum permissible current density of the treatment signal is very low and in practice it is assumed that a maximum value of 0.2 mA/cm$^2$ is still safe. As a result, only a small amount of substance can be introduced into the patient's body per unit time and the treatment takes a relatively long time. In addition, the treatment signal in this form causes such a high skin stress that a daily repetition of the treatment is virtually ruled out.

Another known treatment signal is formed by a pulse current in the form of a half-wave or full-wave rectified sinusoidal signal, which also has the drawback that a burning sensation can be induced in the patient and cauterisation of the skin also occurs.

Moreover, the duty cycle of said signal is appreciably less than 100%, as a result of which a relatively small quantity of substance can be introduced into the body per unit time, with the result that a longer treatment time is necessary and, consequently, a high skin stress occurs again. In addition, the treatment signal in this form has the drawback that such current forms are usually also used for other therapies, with the result that a combination effect occurs, the consequences of which are incalculable.

Finally, a device is also known in which a treatment signal is generated which comprises a depolarising alternating current which is made up of a positive pulse and a smaller negative pulse or vice versa. The duty cycle of this treatment signal is appreciably less than 100%, as a result of which long treatment times and high current densities are necessary. In addition, the negative pulse would result in an inverse effect to the positive pulse, thereby reducing the efficiency of the treatment further.

The object of the invention is to provide a device of the type mentioned in the introduction, in which the disadvantages mentioned are eliminated in a simple and expedient manner.

For this purpose, the device according to the invention has the characteristic that the signal generator generates as treatment signal a pulsed direct current with a duty cycle of at least 80%.

In this manner, a device is obtained which makes possible a particularly expedient iontophoresis treatment of the patient, with a high efficiency for the introduction of the substance being achieved by the relatively high duty cycle. Surprisingly, it has been found that the treatment signal generated by the device according to the invention does not induce any burning sensation in the patient, with the result that a relatively high current density can be used and, consequently, more substance can be introduced in the same treatment time. In practical tests it has been found that no cauterisation of the skin occurs. As a result of the low skin stress, the patient can be treated regularly, if necessary daily.

The invention is explained in greater detail below with reference to the drawing, which shows an exemplary embodiment.

Figure 1:
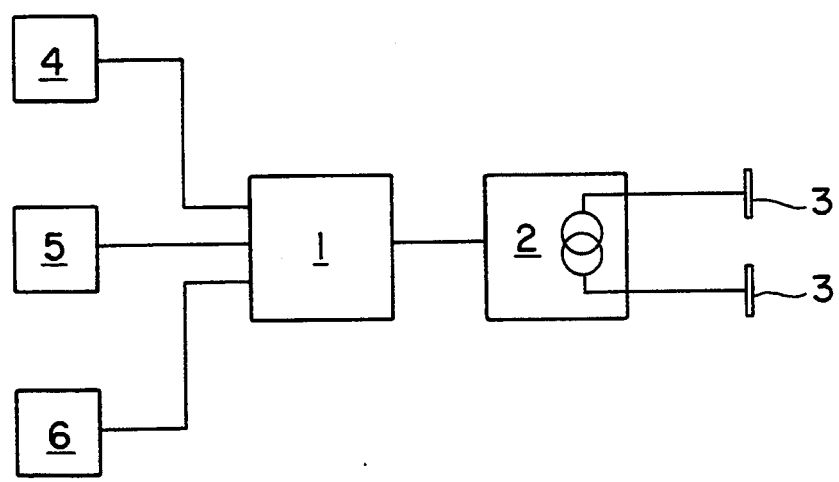
FIG. 1 is a highly simplified block diagram of an embodiment of the device according to the invention.

FIG. 1 shows a highly simplified block diagram of a device for carrying out an iontophoresis treatment on a patient, which device is provided with a signal generator 1 for generating a treatment signal and an output stage 2 which can be connected to the patient by means of two diagrammatically indicated electrodes 3. As is indicated in FIG. 1, the output of the output stage 2 is designed as a current source. The treatment signal generated by the signal generator 1 is a pulsed direct current or rectangular pulse train, the on/off ratio or duty cycle of the signal per cycle being very high, that is to say at least 80%.

The current density, the frequency and the duty cycle of the treatment signal can be set by means of a suitable setting device 4, 5 or 6, respectively. In this connection, the duty cycle can preferably be set between 90 and 98%. Satisfactory treatment results can already be achieved with a duty cycle or at least 80%.

The frequency of the treatment signal can be set by means of the setting device 5 to a value upwards of at least 1 kHz and is preferably set in the region of 4–8 kHz.

Tests have shown that the current density of the treatment signal can, without difficulty, be set a factor of 5 or more higher than in the known device, that is to say to a value of 1 mA/cm$^2$ or higher.

Figure 2:
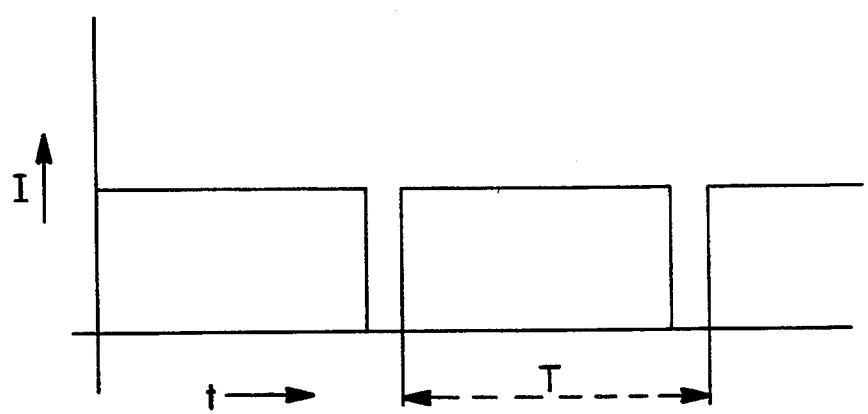
FIG. 2 shows the current form of the treatment signal of the device according to FIG. 1.

An example of the current form of the treatment signal of the device described is shown very diagrammatically in FIG. 2, the cycle of the signal being indicated by T. It is pointed out that the current form will in practice differ more or less from the ideal square shape shown.

The treatment signal in this form has important advantages. The duty cycle can be very high, in the region of 90–98%, as a result of which a high efficiency is achieved in the introduction of substances into the body by means of the treatment. No burning sensation occurs in the patient, with the result that high current densities can be used, as a result of which more drug can be introduced into the patient in a certain treatment period than is possible in the case of the known device. Tests have shown that no cauterisation of the skin occurs. As a result, the treatment can be carried out much more frequently, if necessary even daily.

The invention is not restricted to the embodiment described above, which may be varied in various ways within the scope of the invention.

I claim:

1. A device for effecting iontophoresis treatment on a patient, which comprises a signal generator for generating a treatment signal and having an output stage including two electrodes for connection to said patient, said signal generator generating a treatment signal of a pulsed direct current at a frequency of at least 1 kHz with a duty cycle of said pulsed direct current being greater than 80%.

2. The device for effecting iontophoresis treatment as defined in claim 1 wherein said duty cycle of said pulsed direct current is between 90 to 98%.

3. The device for effecting iontophoresis treatment as defined in claim 2 wherein said frequency of said pulsed direct current is from 4–8 kHz.

4. The device for effecting iontophoresis treatment as defined in claim 1, 2 or 3 wherein said output stage includes output means acting as current source.

5. The device for effecting iontophoresis treatment as defined in claim 4 and further including means for setting said current density, said frequency and duty cycle of said pulsed direct current.

* * * * *